US006566555B2

(12) United States Patent
Thiele et al.

(10) Patent No.: US 6,566,555 B2
(45) **Date of Patent: *May 20, 2003**

(54) PROCESS FOR PREPARING OXIMES

(75) Inventors: Georg Friedrich Thiele, Hanau (DE); Steffen Hasenzahl, Maintal (DE); Thomas Schiffer, Haltern (DE)

(73) Assignee: Degussa AG, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/962,193

(22) Filed: Sep. 26, 2001

(65) Prior Publication Data

US 2002/0058840 A1 May 16, 2002

(30) Foreign Application Priority Data

Sep. 26, 2000 (DE) ........................................ 100 47 435

(51) Int. Cl.[7] .................... C07C 249/00; C07C 251/00; C07C 259/00; C07C 291/00

(52) U.S. Cl. ....................... 564/262; 564/253; 564/258; 564/259; 564/260; 564/261; 564/263; 564/264

(58) Field of Search ................................ 564/253, 258, 564/262

(56) References Cited

U.S. PATENT DOCUMENTS 4,163,756 A * 8/1979 Armor et al.
4,265,834 A * 5/1981 Birkenstock et al.
4,410,510 A 10/1983 Taramasso et al.
4,794,198 A 12/1988 Roffia et al.
5,498,793 A * 3/1996 Mantegazza et al.
5,684,201 A * 11/1997 Rieber et al.

FOREIGN PATENT DOCUMENTS

EP 0 208 311 1/1987
EP 0267362 * 5/1988
EP 0 299 430 1/1989
EP 0 655 278 5/1995

OTHER PUBLICATIONS

Bruno Notari, Microporous Crystalline Titanium Silicates, Advances in Catalysis, vol. 41, 1996, pp., 253–334.
Peter T. Taney, et al., Titanium–containing mesoporous molecular sleves for catalytic oxidation of aromatic compounds, Letters to Nature, vol. 386, Mar. 24, 1994, pp. 321–323.

* cited by examiner

*Primary Examiner*—James O. Wilson
*Assistant Examiner*—Traviss C. McIntosh
(74) *Attorney, Agent, or Firm*—Oblon, Spivak, McClelland, Maier & Neustadt, P.C.

(57) ABSTRACT

Oximes are prepared by reacting carbonyl compounds, hydrogen peroxide and ammonia in the presence of a catalyst system comprising a catalyst comprising titanium, silicon and oxygen and a cocatalyst comprising an acidic solid comprising an organic or inorganic support material, where either the support material itself has Lewis-acid or Brönsted acid properties, or Lewis-acid or Brönsted-acid functional groups are applied to the support material.

23 Claims, No Drawings

PROCESS FOR PREPARING OXIMES

BACKGROUND OF THE INVENTION

1. Field of the Invention

The present invention relates to a catalytic process for preparing oximes. In this process, a carbonyl compound, preferably a cycloalkanone having from 7 to 20 carbon atoms, is reacted in the liquid phase with ammonia and hydrogen peroxide (ammoximation), over a heterogeneous catalyst system comprising two or more components of which at least one of the components comprises at least one porous, titanium-containing solid, and at least one second component comprises an acidic solid.

2. Discussion of the Background

European patent applications EP-A-0 208 311, EP-A-O 267 362 and EP-A-0 299 430 and U.S. Pat. No. 4,794,198, each of which is herein incorporated by reference, describe the preparation and activation of a catalyst based on titanium, silicon and oxygen, and its use for the synthesis of oximes from aldehydes or ketones, for example cyclohexanone, by reaction with hydrogen peroxide and ammonia. The catalysts usually have a silicon:titanium ratio of greater than 30. A typical representative catalyst is the titanium silicalite TS1.

While the synthesis of relatively small aliphatic and cycloaliphatic oximes from ketones having up to 6 carbon atoms, for example, cyclopentanone and cyclohexanone, gives good results for numerous titanium silicalite catalysts, prepared and activated as described in the above mentioned documents, the results are significantly poorer when larger or more sterically hindered carbonyl compounds, such as acetophenone and cyclododecanone, are used. In particular, the reaction rate, the percent conversion of carbonyl compound used, and the hydrogen peroxide selectivity ($H_2O_2$ used for the ammoximation/total amount of $H_2O_2$ required·100%) are unsatisfactory in these experiments.

In the examples of EP-A-O 267 362, conversions of over 90% at a peroxide loss of below 10% are achieved for cyclohexanone (Examples 22 and 24). Comparable reaction conditions using acetophenone give conversions of only 50.8% at a peroxide loss of 48.9%. The reaction of cyclododecanone is also claimed in the cited application, but no specific example is provided with regard to the conversion and peroxide loss obtained when reacting cyclododecanone.

The significantly poorer results obtained for large or sterically hindered carbonyl compounds can be attributed, inter alia, to the inability of large carbonyl compounds such as cyclododecanone to penetrate, or their ability to penetrate only slowly, through the pores of the titanium silicalite catalyst. This can lead to spatial separation of the substeps of hydroxylamine formation (1) and oximation of the ketone (2) (in the reaction equations shown below for cyclododecanone (CDON)).

The decomposition of hydroxylamine by reaction with hydrogen peroxide, formally represented by the stoichiometric equation (3), can occur to a considerable extent as a competing reaction, which reduces the productivity of the reaction and the hydrogen peroxide selectivity.

$$NH_3+H_2O_2 \rightarrow H_2O+NH_2OH \quad (1)$$

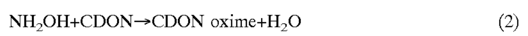

$$NH_2OH+CDON \rightarrow CDON\ oxime+H_2O \quad (2)$$

$$2\ NH_2OH+H_2O_2 \rightarrow 4\ H_2+N_2 \quad (3)$$

German patent application DE 195 21 011 A1 (corresponding to U.S. Pat. No. 5,498,793), describes an amorphous silicon dioxide cocatalyst for the ammoximation of acetophenone and cyclododecanone, in which the addition of amorphous silicon dioxide provides for an increase in the conversion of cyclododecanone after a reaction time 8 hours to 85.5% or 85.2% (DE 195 21 011, Examples 5 and 6) compared to 76.6% without the cocatalyst. The peroxide yield at the same time increased from 65.8% to 71.4% or 72.3%. This process leads to a slight improvement in conversion and peroxide yield, but it also has a number of disadvantages which would make it uneconomical for industrial use:

The amount of catalyst and cocatalyst based on the ketone used is very high in the examples, namely up to 25% by weight in each case, for reactions using cyclododecanone as a starting material.

Despite the high catalyst concentration, the conversion rate is low and the reaction is slow.

Even after a total reaction time of 8 hours, the oxime yield is still far from complete conversion (i.e., complete conversion means an oxime yield of about 99%, preferably above 99.5%).

The mean conversion rate over a reaction time of 8 hours is 7.10 to 7.3 mg of oxime/(g of cat·min) compared to 6.38 mg of oxime/(g of cat·min) without the amorphous silicon dioxide cocatalyst.

For relatively large rings such as, for example, cyclododecanone, high conversion rates, which lead to complete conversion, are very important for industrial applications, because as the molecular weight increases, it is technically difficult to separate the unreacted ketone from the corresponding oxime.

SUMMARY OF THE INVENTION

It is therefore an object of the present invention to provide a process in which the ammoximation proceeds with virtually complete conversion combined with a high conversion rate and good peroxide yield. The percent conversion of the carbonyl compound to an oxime should, where possible, be so high that a subsequent reaction of the carbonyl compound with an aqueous hydroxylamine solution may be dispensed with. It has surprisingly found that this object can be achieved by reacting a carbonyl compound, hydrogen peroxide and ammonia in the presence of an acidic cocatalyst together with the titanium-containing catalyst. In particular, it has been found that the conversion rate can be significantly improved thereby.

DETAILED DESCRIPTION OF THE INVENTION

Thus, an embodiment of the present invention provides for reacting a carbonyl compound, hydrogen peroxide and ammonia in the presence of a catalyst system comprising a catalyst and a cocatalyst, wherein the catalyst comprises at least one crystalline microporous or mesoporous solid comprising titanium, silicon and oxygen, and the cocatalyst comprises an acidic solid comprising an organic or inorganic support material, and the support material itself has Lewis-acid or Brönsted-acid properties, or Lewis-acid or Brönsted-acid functional groups are physically or chemically applied to the support material.

The catalyst is preferably a compound comprising titanium, silicon and oxygen, and having a porous structure, for example titanium silicalites. The porous structure may be either microporous and/or mesoporous structures. By microporous structure, we mean a structure having pores sizes which are less than 2 nm. By mesoporous structure, we mean a structure having pore sizes in the range of approximately 2 to 50 nm. Non-limiting examples of microporous titanium silicalites are the types TS1 and Ti-beta. Non-limiting examples of mesoporous structures are the titanium silicalites of the type Ti-MCM41 and Ti-HMS. The preparation of TS1 type silicalites is described, for example, in U.S. Pat. No. 4,410,501 and Bruno Notari, "Microporous Crystalline Titanium Silicates", Advances in Catalysis, vol. 41 (1996), pp. 253–334; the preparation of Ti-beta is described, for example, in Spanish Patent 2037596; the preparation of Ti-MCM41 is described, for example, in EP 0655278; and the preparation of Ti-HMS is described, for example, by Tanev et al, *Nature,* 368 (1994), pp. 321–323, each of which is incorporated herein by reference.

Suitable cocatalysts are solids which themselves have Lewis and/or Brönsted-acid properties on their surface or in the pores thereof. Non-limiting examples of such inorganic cocatalysts which have Lewis and/or Brönsted acid properties are acidic aluminum oxides and acidic, activated aluminosilicates such as bentonite, montmorillonite and kaolinite.

Alternatively, the cocatalysts may have Lewis acid and/or Brönsted acid functional groups, either chemically or physically applied thereto. Cocatalysts having chemically applied acid groups include sulfonated or phosphonated resins. Alternatively, the cocatalyst may be an inert solid support having a physically applied acidic coating, such as a coating of a sulfonated resin or an acidic inorganic material, such as acidic aluminum oxides and acidic, activated aluminosilicates such as bentonite, montmorillonite and kaolinite on an inert solid support. The inert solid support may be any organic or inorganic material which is not affected by the ammoximation reaction conditions or reagents used. Non-limiting examples of cocatalysts based on organic support materials which have Lewis and/or Brönsted acid functional groups are acid and strong acid ion exchange resins such as sulfonated polystyrene ion-exchange resins, for example Amberlyst 15, or sulfonated perfluorocarbon ion-exchange resins such as Nafion NR50.

The catalyst and cocatalyst may have any physical form. For example, both may independently be a solid such as a powder or a shaped body. A shaped body is prepared by pressing a powder of the catalyst and/or cocatalyst together into the desired shape, for example using a press or by an extrusion process. The weight ratio of catalyst to cocatalyst is usually in the range from 0.1:1 to 10:1, preferably 0.5:1 to 4:1.

If the catalyst and/or cocatalyst are used as shaped bodies, it is possible for additional additives, such as binders, to be present in the shaped body. Non-limiting examples of such additives are neutral and/or weakly acidic silicates, aluminosilicates and clay minerals. In a particularly preferred variant of the invention, an acidic solid simultaneously performs the functions of a cocatalyst and of a binder in a titanium silicalite shaped body. Of course, both the catalyst and the cocatalyst can each consist of mixtures of two or more components.

The process of the present invention provides for the ammoximation of large carbonyl compounds and preferably of large cyclic ketones, in particular of rings having from 7 to 20 carbon atoms, most preferably of cyclooctanone and cyclododecanone, using hydrogen peroxide and ammonia.

The ammoximation of cycloalkanones according to the process of the present invention proceeds highly selectively. At complete conversions, the selectivity of forming the oxime is, according to analysis by gas chromatography (GC), over 99% for both cyclooctanone and cyclododecanone. If technical-grade cyclododecanone is used, the only by-products detected in the gas chromatogram are traces of cyclododecane and cyclododecanol which were originally present as contaminants in the cyclododecanone. In a few cases, laurolactam was found as a further by-product, in concentrations of <0.1%.

If the reaction is carried out in a solvent, the solvent may be any compound which is stable toward hydrogen peroxide and ammonia, and sufficiently solvates both the carbonyl compound and the oxime product formed. The solvent may be miscible with water, but does not have to be. The preferred solvents are aliphatic alcohols which are miscible or partially miscible with water, selected from among $C_1$–$C_6$-aliphatic or cycloaliphatic alcohols, for example methanol, ethanol, n-propanol, isobutanol, tert-butanol or tert-amyl alcohol. Particularly useful solvents for the ammoximation of cyclododecanone are methanol, ethanol and tert-butanol.

Hydrogen peroxide is preferably used as an aqueous solution in commercially available concentrations (30 to 70 wt. %, preferably at least 35 wt. %). Ammonia is introduced into the reactor either as a concentrated, aqueous solution (preferably ≧20%) or preferably as a gas. When the ammonia is introduced in gaseous form and highly concentrated peroxide solutions are used, advantages result from the reduced amount of water which has to be separated from the solvent during work-up of the reaction mixture.

The reaction temperature in the ammoximation according to the present invention is from 20° C. to 150° C., preferably from 50° C. to 120° C. and particularly preferably from 60° C. to 100° C. The reactor is operated either at autogenous pressure, namely the pressure established as a result of the sum of the partial pressures at the respective reaction temperatures, or at increased pressure, preferably from 1 to 10 bar. The increased pressure can be provided by pressurizing the reactor with ammonia gas or an inert gas such as nitrogen. If the reactor is closed, the pressure increases slowly during the reaction due to formation of gaseous decomposition products (in particular nitrogen) during secondary reactions. It is advantageous to operate the reactor isobarically by allowing gaseous decomposition products to escape in a controlled manner via a gentle waste gas stream and replacing the ammonia which also escapes by means of a regulating valve.

Gaseous ammonia present in the waste gas stream can be collected by condensation and returned to the process.

In the ammoximation reaction, the carbonyl compound and hydrogen peroxide can each be introduced into the reactor either continuously or discontinuously. Since decomposition reactions as described by equation (3) always occur, complete conversion of the carbonyl compound requires the use of a stoichiometric excess of peroxide. The amount of excess peroxide used can be minimized by means of appropriate reaction conditions and by use of catalyst systems according to the present invention. Experimentally, it has been found to be advantageous either to charge the carbonyl compound into the reactor at the beginning of the reaction (i.e., discontinuous addition) or to meter it into the reactor in molar amounts corresponding to the amount of hydrogen peroxide added (i.e., continuous addition), and to add the necessary excess of peroxide as required by the consumption of hydrogen peroxide after addition of the carbonyl compound is complete.

Having generally described this invention, a further understanding can be obtained by reference to certain specific examples which are provided herein for purposes of illustration only, and are not intended to be limiting unless otherwise specified.

EXAMPLES

In all examples, fresh catalyst (titanium silicalite TS1, Degussa-Hüs AG) was used, which was not additionally activated prior to carrying out the reaction. After the reaction, the pulverulent catalyst was recovered from the crude product mixture by pressure filtration.

Examples 1–4 were carried out at a reaction temperature of 60° C. in a tert-butanol solvent, using a heated 100 ml glass pressure reactor fitted with a sparging stirrer. In each example, the reaction was stopped after a total time of somewhat above 5 hours. The cyclododecanone conversion was determined by GC, and the peroxide content was determined by redox titration with cerium sulfate.

Example 1 (Comparative Experiment)

1.0 g of titanium silicalite TS1 (Degussa-Hüs AG), 9.1 g of cyclododecanone, 1.5 g of diglyme (diethylene glycol dimethyl ether) as internal standard for gas chromatography and 38.9 g of 95% by weight tert-butanol were placed in a reactor. The reactor was flushed with ammonia gas and set to a gauge pressure of ammonia of 1.0 bar. After the reactor had been heated to 60° C., 6.8 g of 50.7% by weight hydrogen peroxide solution was metered into the reactor over a period of 185 minutes while the reaction mixture was stirring vigorously. After a post-reaction time of 2 hours at 60° C., a hydrogen peroxide conversion of 81% and a cyclododecanone conversion of 70% was obtained. The only product of the reaction found by GC analysis was cyclododecanone oxime.

Example 2 (Comparative Experiment)

The same procedure as in Example 1 was carried out, except that in addition to the titanium silicalite catalyst (1.0 g of T 1, Degussa-Hüs AG), 1.0 g of silica gel 60 (Merck), as described in DE 195 21 011 A1, was added to the reactor. A hydrogen peroxide conversion of 97% and cyclododecanone conversion of 60% was obtained. The only product of the reaction found by GC analysis was cyclododecanone oxime.

Example 3

The same procedure as in Example 1 was carried out, except that the catalyst system used was a mixture of 0.8 g of pulverulent titanium silicalite catalyst (TS1, Degussa-Hüs AG) and 0.2 g of Pural SB $Al_2O_3$ cocatalyst (Condea). A hydrogen peroxide conversion of 86% and a cyclododecanone conversion of 79% was obtained. The only product of the reaction found by GC analysis was cyclododecanone oxime.

Example 4

The same procedure as in Example 1 was carried out, except that the catalyst system used was 1.0 g of a catalyst system produced by extrusion of a pulverulent titanium silicalite catalyst (1.0 g of TS1, Degussa-Hüs AG) with 20% by weight of Pural SB $A1_2O_3$ cocatalyst, drying the extrudate, calcination of the extrudate at 550° C. and pulverization. A hydrogen peroxide conversion of 97% and a cyclododecanone conversion of 84% was obtained. The only product of the reaction found by GC analysis was cyclododecanone oxime.

Examples 5 to 11 demonstrate the complete conversion of cyclododecanone under optimized reaction conditions at 80° C., using an ethanol solvent. The experiments were carried out in a heated 1.6 l glass pressure reactor fitted with a sparging stirrer (500 rpm) and a pressure regulator. Samples were removed from the reaction mixture at regular intervals and analyzed. The percent conversion of cyclododecanone was determined by gas chromatography, and the percent conversion of hydrogen peroxide was determined by redox titration.

Example 5 (Comparative Example, C)

2.5 g of catalyst (TS1, Degussa-Hüs AG) were suspended at 40° C. in a solution of 62.7 g (344 mmol) of cyclododecanone and 488 g of ethanol. The reactor was heated to 80° C. and depressurized to 0.1 bar. Ammonia gas was subsequently injected into the reactor until the pressure was 1.6 bar, which required the addition of 13 g (765 mmol) of ammonia. This corresponds to 2.2 molar equivalents of ammonia based on cyclododecanone. During the reaction, the pressure was kept constant by means of a gentle waste gas stream. Ammonia gas which escaped in this stream (about 2 g/4 h) was replaced. Over a period of 2 hours, 2.04 equivalents (702 mmol) of hydrogen peroxide were metered into the reactor as an aqueous solution (50.4% by weight $H_2O_2$). After the addition of peroxide was complete, the reaction mixture was left to react further for another 120 minutes.

After 240 minutes, the conversion of cyclododecanone was 99.80%, and 1.96 equivalents of $H_2O_2$ were consumed. This corresponds to a peroxide selectivity of 50.9%. Additional results are shown in Tables 1 and 2.

Example 6

The same procedure as in Example 5 was carried out, except the catalyst system used was 2.5 of titanium silicalite (TS1, Degussa-Hüs AG) catalyst and 1.25 g of aluminum oxide (Aldrich, activated, acidic, ~50 mesh, CAMAG 504-C-I, surface area: 155 $m^2/g$) cocatalyst. Over a period of 2 hours, 1.99 equivalents of $H_2O_2$ were metered into the reactor. After 240 minutes, the conversion of cyclododecanone was 99.77%, and 1.91 equivalents of $H_2O_2$ were consumed. This corresponds to a peroxide selectivity of 52.2%. Additional results are shown in Tables 1 and 2.

Example 7

The same procedure as in Example 5 was carried out, except the catalyst system used was 2.5 of titanium silicalite (TS1, Degussa-Hüs AG) catalyst and 2.5 g of aluminum oxide (Aldrich, as in Example 6) cocatalyst. Over a period of 2 hours, 1.88 equivalents of $H_2O_2$ were metered into the reactor. After 240 minutes, the conversion of cyclododecanone was 99.76%, and 1.76 equivalents of $H_2O_2$ were consumed. This corresponds to a peroxide selectivity of 56.7%. Additional results are shown in Tables 1 and 2.

Example 8

The same procedure as in Example 5 was carried out, except the catalyst system used was 2.5 of titanium silicalite (TS1, Degussa-Hüs AG) catalyst and 5.0 g of aluminum oxide (Aldrich, as in Example 6) cocatalyst. Over a period of 2 hours, 2.04 equivalents of $H_2O_2$ were metered into the reactor. After 240 minutes, the conversion of cyclododecanone was 99.85%, and 1.96 equivalents of $H_2O_2$ were consumed. This corresponds to a peroxide selectivity of 51.0%. Additional results are shown in Tables 1 and 2.

Example 9

The same procedure as in Example 5 was carried out, except the catalyst system used was 2.5 g of titanium silicalite (TS1, Degussa-Hüs AG) catalyst and 2.5 g of montmorillonite (Engelhard, activated acidic, BET surface area: 300 $m^2/g$) cocatalyst. Over a period of 2 hours, 2.04 equivalents of $H_2O_2$ were metered into the reactor. After 240 minutes, the conversion of cyclododecanone was 98.73%, and 1.99 equivalents of $H_2O_2$ were consumed. This corresponds to a peroxide selectivity of 49.8%. Additional results are shown in Tables 1 and 2.

Example 10

The same procedure as in Example 5 was carried out, except the catalyst system used was 2.5 of titanium silicalite (TS1, Degussa-Hüs AG) catalyst and 2.5 g of Nafion NR 50 (Fluka) cocatalyst. Over a period of 2 hours, 2.04 equivalents of H202 were metered into the reactor. After 240 minutes, the conversion of cyclododecanone was 99.84%, and 1.94 equivalents of $H_2O_2$ were consumed. This corresponds to a peroxide selectivity of 51.5%. Additional results are shown in Tables 1 and 2.

Example 11 (Comparative Example, C)

The same procedure as in Example 5 was carried out, except the catalyst system used was 2.5 of titanium silicalite (TS1, Degussa-Hüs AG) catalyst and 2.5 g of amorphous silicon dioxide (silica gel, Merck) cocatalyst. Over a period of 2 hours, 2.04 equivalents of $H_2O_2$ were metered into the reactor. After 4 hours, the conversion of cyclododecanone was 99.79%, and 1.98 equivalents of $H_2O_2$ were consumed. This corresponds to a peroxide selectivity of 50.4%. Additional results are shown in Tables 1 and 2.

TABLE 1

Conversion of CDON over the reaction time

| Example No. (cocatalyst) | 60 min % | 120 min % |
|---|---|---|
| 5 (none) (C) | 49.27 | 83.33 |
| 6 (1.25 g of aluminum oxide) | 55.58 | 95.27 |
| 7 (2.5 g of aluminum oxide) | 58.38 | 92.50 |
| 8 (5.0 g of aluminum oxide) | 60.80 | 93.35 |
| 9 (2.5 g of montomorrillonite) | 56.41 | 93.86 |
| 10 (2.5 g of Nafion) | 56.77 | 88.35 |
| 11 (2.5 g of silica gel) (C) | 50.34 | 85.82 |

TABLE

Conversion rate for oxime formation

| Example No. (cocatalyst) | Conversion rate after 60 min mg of oxime/(g of TS1 · min) |
|---|---|
| 5 (none) (C) | 222.9 |
| 6 (1.25 g of aluminum oxide) | 251.5 |
| 7 (2.5 g of aluminum oxide) | 264.1 |
| 8 (5.0 g of aluminum oxide) | 275.1 |
| 9 (2.5 g of montmorillonite) | 255.2 |
| 10 (2.5 g of Nafion) | 256.8 |
| 11 (2.5 g of silica gel) (C) | 227.8 |

Example 12 (Comparative Example)

The same procedure as in Example 5 was carried out, except that in place of cyclododecanone, 43.67 g (346 mmol) of cyclooctanone was placed in the reactor. Over a period of 2 hours, 2.04 equivalents of $H_2O_2$ were metered in, and the mixture was subsequently stirred for another 1 hour. After 60 minutes, 63.6 g of cyclooctanone had been reacted to cyclooctanone oxime, which corresponds to a conversion rate of 207.20 mg of oxime/(g TS1.·min). After 180 minutes, the conversion of cyclooctanone was 99.7%, and a total of 1.99 equivalents of $H_2O_2$ were consumed. This corresponds to a peroxide selectivity of 50.1%.

Example 13

The same procedure as in Example 12 was carried out, except 2.5 g of aluminum oxide (Aldrich, as in Example 6) cocatalyst was also added. After 60 minutes, 71.9% of cyclooctanone had been reacted to cyclooctanone oxime, which corresponds to a conversion rate of 234.3 mg of oxime/(g TS1.·min). After 180 minutes, the conversion was 100%, and a total of 2.01 equivalents of $H_2O_2$ were consumed. This corresponds to a peroxide selectivity of 49.8%.

Example 14

Experiment 13 was repeated. Over a period of 2 hours, 1.51 equivalents of $H_2O_2$ were metered in, and the mixture was subsequently stirred for another 1 hour. After 180 minutes, the conversion of cyclooctanone was 99.7%, and 1.50 equivalents of $H_2O_2$ were consumed. This corresponds to a peroxide selectivity of 66.5%.

Example 15: Fixed-Bed Reactor

The experimental set-up of Example 5 was supplemented with a fixed-bed reactor fitted with a circulation pump (150 ml/min). 30 g of shaped bodies (pellets, 1 mm diameter), produced in an extruder from 50% by weight of titanium silicalite (TS1, Degussa-Hüs AG) catalyst and 50% by weight of Pural SB aluminum oxide cocatalyst by a method analogous to Example 4, was used as a fixed bed catalyst system.

The reaction was carried out at a temperature of 80° C. at a constant pressure of 1.6 bar in manner analogous to the procedure of Example 5. The reactor circuit was charged with 62.7 g of cyclododecanone in 488 g of ethanol. Hydrogen peroxide (50% aqueous solution) was fed into the reactor circuit upstream of the fixed-bed reactor. Over a period of 4 hours, 1.94 equivalents of hydrogen peroxide were metered into the reactor. After peroxide addition was complete, the mixture as stirred for another 1 hour.

After 300 minutes, the conversion of cyclododecanone was 99.7% at a peroxide consumption of 1.90 equivalents. This corresponds to a peroxide selectivity of 52.5%.

The priority document of the present application, German application 10047435.7, filed Sep. 26, 2000, is incorporated herein by reference.

Obviously, numerous modifications and variations on the present invention are possible in light of the above teachings. It is therefore to be understood that within the scope of the appended claims, the invention may be practiced otherwise than as specifically described herein.

What is claimed as new and is intended to be secured by Letters Patent is:

1. A process for preparing oximes comprising:

reacting a carbonyl compound, hydrogen peroxide and ammonia in the presence of a catalyst system comprising a catalyst and a cocatalyst, wherein the catalyst comprises at least one crystalline microporous and/or mesoporous solid comprising titanium, silicon and oxygen, and the cocatalyst comprises at least one acidic solid selected from the group consisting of acidic aluminum oxides and acidic, activated aluminosilicates alone or on an organic or inorganic support.

2. The process of claim 1, wherein the carbonyl compound is a cyclic ketone having from 7 to 20 carbon atoms.

3. The process of claim 1, wherein the carbonyl compound is cyclooctanone or cyclododecanone.

4. The process of claim 1, wherein said reacting is in the presence of an organic solvent.

5. The process of claim 4, wherein the organic solvent is an alcohol which is miscible or partially miscible with water and is selected from the group consisting of $C_1$–$C_6$ aliphatic or cycloaliphatic mono alcohols.

6. The process of claim 5, wherein the alcohol is methanol, ethanol or tert-butanol.

7. The process of claim 1, wherein said reacting takes place at a temperature of from 20° C. to 150° C.

8. The process of claim 1, wherein said reacting takes place at a pressure of from 1 to 10 bar.

9. The process of claim 1, wherein said reacting takes place in a reactor, and ammonia is fed in gaseous form into the reactor.

10. The process of claim 1, wherein the hydrogen peroxide is in the form of a solution having a hydrogen peroxide concentration of a least 35% by weight.

11. The process of claim 1, wherein the catalyst is a titanium silicalite.

12. The process of claim 1, wherein the cocatalyst is an acidic solid selected from the group consisting of a bentonite, a montmorillonite or a kaolinite.

13. The process of claim 1, wherein the cocatalyst is an organic solid comprising an acid ion exchange resin.

14. The process of claim 1, wherein the weight ratio of catalyst to cocatalyst is from 0.1:1 to 10:1.

15. The process of claim 1, wherein the catalyst and cocatalyst are in the form of a powder.

16. The process of claim 1, wherein the catalyst system comprises a catalyst and cocatalyst in the form of a shaped body.

17. The process of claim 16, wherein the cocatalyst functions as a binder for the shaped body.

18. The process of claim 16, wherein the shaped body further comprises a binder selected from the group consisting of neutral silicates, acidic silicates, aluminosilicates, clay minerals, and mixtures thereof.

19. The process of claim 1, wherein the carbonyl compound is added continuously during said reacting.

20. The process of claim 1, wherein the carbonyl compound is added discontinuously during said reacting.

21. The process of claim 1, wherein the hydrogen peroxide is added continuously during said reacting.

22. The process of claim 1, wherein the hydrogen peroxide is added discontinuously during said reacting.

23. The process of claim 1, wherein the weight ratio of catalyst to cocatalyst is from 0.5:1 to 4:1.

* * * * *